(12) United States Patent
Zhang

(10) Patent No.: US 10,588,577 B2
(45) Date of Patent: Mar. 17, 2020

(54) PATIENT SIGNAL ANALYSIS BASED ON AFFINE TEMPLATE MATCHING

(71) Applicant: Siemens Medical Solutions USA, Inc., Malvern, PA (US)

(72) Inventor: Hongxuan Zhang, Palatine, IL (US)

(73) Assignee: Siemens Healthcare GmbH, Erlangen (DE)

( * ) Notice: Subject to any disclaimer, the term of this patent is extended or adjusted under 35 U.S.C. 154(b) by 806 days.

(21) Appl. No.: 14/609,083

(22) Filed: Jan. 29, 2015

(65) Prior Publication Data

US 2016/0220190 A1 Aug. 4, 2016

(51) Int. Cl.
| | |
|---|---|
| *A61B 5/00* | (2006.01) |
| *A61B 5/021* | (2006.01) |
| *A61B 5/026* | (2006.01) |
| *A61B 5/145* | (2006.01) |

(52) U.S. Cl.
CPC ............ *A61B 5/7253* (2013.01); *A61B 5/021* (2013.01); *A61B 5/026* (2013.01); *A61B 5/7246* (2013.01); *A61B 5/7282* (2013.01); *A61B 5/02108* (2013.01); *A61B 5/14542* (2013.01); *A61B 5/4836* (2013.01)

(58) Field of Classification Search
None
See application file for complete search history.

(56) References Cited

U.S. PATENT DOCUMENTS

| | | | |
|---|---|---|---|
| 4,566,463 A | 1/1986 | Taniguchi | |
| 5,279,303 A | 1/1994 | Kawamura | |
| 5,423,326 A | 6/1995 | Wang | |
| 5,553,615 A * | 9/1996 | Carim | A61B 5/14535 356/39 |
| 5,615,684 A | 4/1997 | Hagel et al. | |
| 6,007,491 A | 12/1999 | Ling | |
| 6,050,951 A | 4/2000 | Friedman et al. | |
| 6,071,244 A | 6/2000 | Band | |
| 6,117,075 A | 9/2000 | Barnea et al. | |
| 6,179,783 B1 | 1/2001 | Mohler | |
| 6,186,956 B1 | 2/2001 | McNamee | |
| 6,224,553 B1 | 5/2001 | Nevo et al. | |
| 6,348,038 B1 | 2/2002 | Band | |
| 6,485,429 B2 | 11/2002 | Forstner | |

(Continued)

FOREIGN PATENT DOCUMENTS

EP 2072012 6/2009

OTHER PUBLICATIONS

Biometrics, Biomathematics and the Morphometric Synthesis; Fred L. Bookstein; Bulletin of Mathematical Biology, vol. 58, No. 2, pp. 313-365, 1996.*

(Continued)

*Primary Examiner* — Kaylee R Wilson
*Assistant Examiner* — Jay B Shah

(57) ABSTRACT

Disclosed herein is a framework for facilitating patient signal analysis. In accordance with one aspect, the framework performs affine template matching of a region of interest from patient signal data with a baseline signal portion by performing an affine waveform transformation of the region of interest. One or more affine ratios may be determined based on the matched region of interest and the baseline signal portion for generating a report or diagnosis of a cardiac event.

19 Claims, 6 Drawing Sheets

(56) References Cited

U.S. PATENT DOCUMENTS

| | | | |
|---|---|---|---|
| 6,511,436 B1 | 1/2003 | Asmar | |
| 6,511,438 B2 | 1/2003 | Bernstein | |
| 6,514,211 B1 | 2/2003 | Baura | |
| 6,636,754 B1 | 10/2003 | Baura | |
| 6,758,822 B2 | 7/2004 | Romano | |
| 6,929,610 B2 | 8/2005 | Forstner | |
| 7,024,244 B2 | 4/2006 | Muhlenberg | |
| 7,074,192 B2 | 7/2006 | Friedman | |
| 7,220,230 B2 | 5/2007 | Roteliuk | |
| 7,367,949 B2 | 5/2008 | Korhonen | |
| 7,374,541 B2 | 5/2008 | Amitzur | |
| 7,384,395 B2 | 6/2008 | Hatlestsad | |
| 7,413,548 B2 | 8/2008 | Tadokoro | |
| 7,503,896 B2 | 3/2009 | Miele | |
| 7,594,893 B2 | 9/2009 | Tao | |
| 7,704,209 B2 | 4/2010 | Bennett | |
| 7,988,635 B2 | 8/2011 | Cho | |
| 8,374,678 B2 | 2/2013 | Graumann | |
| 8,556,818 B2 | 10/2013 | Joeken | |
| 8,764,670 B2 | 7/2014 | Sawanoi | |
| 2001/0053240 A1* | 12/2001 | Oosawa | G06K 9/6203 382/128 |
| 2006/0104519 A1* | 5/2006 | Stoeckel | G06K 9/6292 382/224 |
| 2007/0265533 A1* | 11/2007 | Tran | A61B 5/021 600/481 |
| 2008/0292194 A1* | 11/2008 | Schmidt | G06T 7/0012 382/217 |
| 2009/0131769 A1* | 5/2009 | Leach | A61B 5/0031 600/309 |
| 2009/0209868 A1 | 8/2009 | Hersh | |
| 2009/0264956 A1* | 10/2009 | Rise | A61B 5/4836 607/45 |
| 2010/0152593 A1 | 6/2010 | Lowe | |
| 2010/0189320 A1* | 7/2010 | Dewaele | G06T 7/0093 382/128 |
| 2010/0204592 A1 | 8/2010 | Hatib | |
| 2010/0280396 A1 | 11/2010 | Zhang | |
| 2012/0179382 A1* | 7/2012 | Zhang | A61B 5/02416 702/19 |
| 2014/0278322 A1* | 9/2014 | Jaramaz | G06F 19/3437 703/11 |
| 2015/0157879 A1* | 6/2015 | Wu | A61N 5/1067 378/8 |
| 2015/0248648 A1* | 9/2015 | Rao | G06Q 10/1053 705/321 |

OTHER PUBLICATIONS

Registration of 3D Point Clouds and Meshes: A Survey From Rigid to Non-Rigid; Tam et al; Journal of Latex Class Files, vol. 6, No. 1, Jan. 2007.*

Affine (distance) ratio from 3 parallel lines; https://sites.math.washington.edu/~king/coursedir/m445w01/syl/class/parallel-affine/affine-line-ratio.html.* https://sites.math.washington.edu/~king/coursedir/m445w01/syl/class/parallel-affine/affine-line-ratio.html—Affine (distance) ratio from 3 parallel lines, 2001 (Year: 2001).*

Parati, "Neural cardiovascular regulation and 24-hour blood pressure and heart rate variability", Annals of NY Academy of Sciences, 783: pp. 47-63, 1996.

Wei Huang, et al., "Engineering analysis of biological variables: An example of blood pressure over 1 day", PNAS Apr. 28, 21998, vol. 95, No. 9, pp. 4816-4821.

* cited by examiner

PATIENT SIGNAL ANALYSIS BASED ON AFFINE TEMPLATE MATCHING

TECHNICAL FIELD

The present disclosure generally relates to systems and methods for patient signal analysis.

BACKGROUND

Hemodynamic data from clinical patient include any patient signal data associated with blood flow and related characteristics, such as blood pressure, blood flow speed, oximetric signal data, etc. Saturation of peripheral oxygen (SPO2) level is an oximetric measurement, which may be non-invasively acquired by optical sensors. Blood pressure (BP) is a mechanical pressure in the blood exerted by circulating blood in blood vessels. There are two types of blood pressure: systolic and diastolic. Both types of blood pressure may be derived either invasively (invasive blood pressure or IBP) or non-invasively (non-invasive blood pressure of NIBP). The systolic blood pressure corresponds to the pressure of the blood when the heart has imparted maximum pressure, while the diastolic blood pressure is the pressure when the heart is in the resting phase.

During each heartbeat, BP varies between a maximum (systolic) and a minimum (diastolic) pressure. The mean BP value decreases as the circulating blood moves away from the heart through arteries, experiences its greatest decrease in small arteries and arterioles, and continues to decrease as the blood moves through the capillaries and back to the heart through veins. The systolic pressure and diastolic pressure signal waveform characteristics (e.g., amplitude, phase, morphology, etc.) may show different kinds of variation due to different cardiac events or arrhythmias. In other words, the mean BP value alone may not be sufficient to differentiate cardiac events based on recognition thresholds. BP is determined by the force and amount of blood pumped, and the size and flexibility of the arteries. Systolic and diastolic arterial BP values are not static, but undergo natural variations from one heartbeat to another and throughout the day (in a circadian rhythm). BP variation may be utilized for monitoring patient healthy status.

Hemodynamic signal data may be used for characterization of cardiac arrhythmias and/or pathological events. Till now, traditional methods of using blood pressure signals focus on stroke volume and cardiac output calculation. Such traditional methods fail to fully capture waveform information from patient blood pressure signal data. In addition, current clinical methods for blood pressure analysis may have different kinds of limitations, such as described in the following.

Current clinical methods utilize only partial hemodynamic information, such as pressure amplitude, time duration, oxygen saturation level, etc. In addition, current hemodynamic diagnostic approaches typically focus on specific parameters, such as systolic-diastolic pressure signal values, without paying attention to the heart rate and cardiac conditions. Some methods purely use amplitude and timing to quantify signal changes, such as maximum amplitude and EoD (end of diastolic)-EoS (end of systolic) timing. During different situations, such as pacing, ablation, asthma, etc., the heart rate and signal strength/shape/latency are not stable, and current diagnostic methods may not be able to efficiently and effectively compare the signals. Further, known methods for blood pressure waveform diagnosis require extensive clinical experience to interpret parameters, calculation accuracy, etc., which may pose a challenge for some users.

Traditional cardiac function analysis typically utilizes electrophysiological signal data (e.g., electrocardiogram or ECG, intracardiac electrogram or ICEG, etc.) for arrhythmia diagnosis. However, electrophysiological signal data are much more easily distorted and affected by electrical noise and bio-artifacts, such as power line noise, patient movement, etc. Hemodynamic signal data may provide better noise immunity and cardiac function analysis stability. Furthermore, there are currently no known sensitive hemodynamic quantitative methods that are well developed for implantable cardiac devices (ICDs). Till now, most ICD instruments still use electrophysiological signal data to monitor, calculate and treat cardiac arrhythmias and pathologies.

SUMMARY

The present disclosure relates to a framework for facilitating patient signal analysis. In accordance with one aspect, the framework performs affine template matching of a region of interest from patient signal data with a baseline signal portion by performing an affine waveform transformation of the region of interest. One or more affine ratios may be determined based on the matched region of interest and the baseline signal portion for generating a report or diagnosis of a cardiac event.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
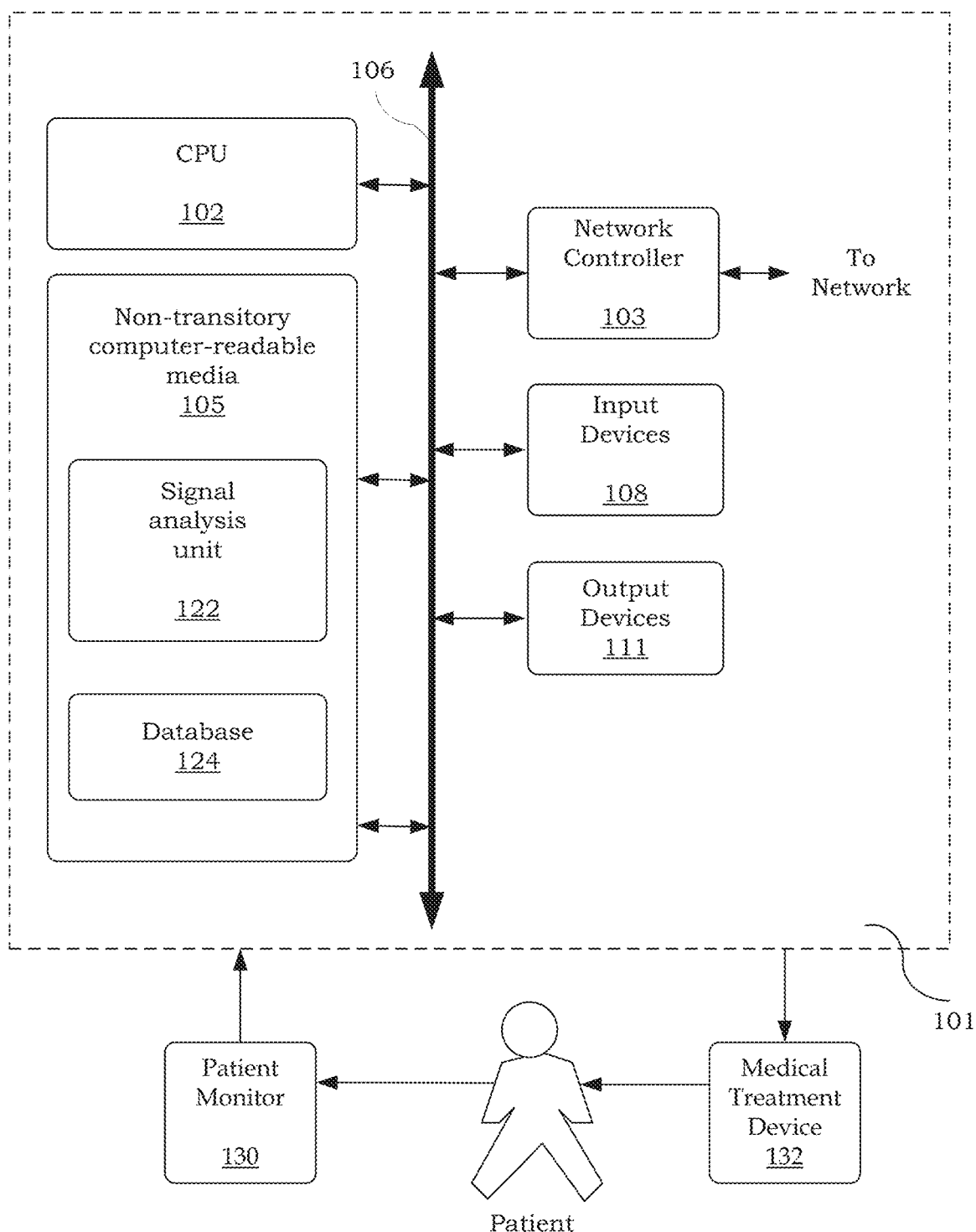
FIG. 1 shows an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

The present framework provides a methodology to analyze patient signal data. In accordance with one aspect, the framework performs hemodynamic mode and pattern analysis for cardiac arrhythmia and pathology detection. The framework may perform the analysis on hemodynamic signal (e.g., blood pressure, oximetric, etc.) waveforms using affine template matching to generate affine ratios that characterize the similarity mode of hemodynamic activity and distortion pattern at different heart rates or cycle lengths.

The present framework advantageously provides an efficient and reliable approach to bridge pressure mode and pattern calculation-based analysis with cardiac arrhythmia diagnosis and status characterization, especially at different heart rates. The affine ratios advantageously facilitate the prediction and tracking of cardiac tissue abnormality at a very early stage, which may greatly reduce the operation risk, treatment cost and complexity of cardiac pathology. By monitoring waveform patterns and modes of multi-channel hemodynamic signal data, the type, time, location, severity and/or trend of a cardiac malfunction or pathological event may be more accurately, sensitively and reliably characterized and diagnosed.

FIG. 1 shows an exemplary system 100 for implementing a method and system of the present disclosure. It is to be understood that, because some of the constituent system components and method steps depicted in the accompanying figures can be implemented in software, the actual connections between the system components (or the method steps) may differ depending upon the manner in which the present framework is programmed. For example, the system 100 may be implemented in a client-server, peer-to-peer (P2P) or master/slave configuration. In such configurations, the system 100 may be communicatively coupled to other systems or components via a network, such as an Intranet, a local area network (LAN), a wide area network (WAN), a P2P network, a global computer network (e.g., Internet), a wireless communication network, or any combination thereof. Given the teachings of the present invention provided herein, one of ordinary skill in the related art will be able to contemplate these and similar implementations or configurations of the present invention.

As shown in FIG. 1, the system 100 may include a computer system 101, a patient monitor 130 and a medical treatment device 132. The computer system 101 may include, inter alia, a central processing unit (CPU) or processor device 102, a non-transitory computer-readable media 105, one or more output devices 111 (e.g., printer, display monitor, projector, speaker, etc.), a network controller 103, an internal bus 106 and one or more input devices 108, for example, a keyboard, mouse, touch screen, gesture and/or voice recognition module, etc. Computer system 101 may further include support circuits such as a cache, a power supply, clock circuits and a communication bus. Various other peripheral devices, such as additional data storage devices and printing devices, may also be connected to the computer system 101.

The present technology may be implemented in various forms of hardware, software, firmware, special purpose processors, or a combination thereof, either as part of a microinstruction code or as part of an application program or software product, or a combination thereof, which is executed via the operating system. In one implementation, the techniques described herein may be implemented as computer-readable program code tangibly embodied in non-transitory computer-readable media 105. Non-transitory computer-readable media or memory device 105 may include random access memory (RAM), read only memory (ROM), magnetic floppy disk, flash memory, and other types of memories, or a combination thereof. The present techniques may be implemented by patient signal analysis unit 122 that is stored in computer-readable media 105. As such, the computer system 101 is a general-purpose computer system that becomes a specific-purpose computer system when executing the computer-readable program code.

The same or different computer-readable media 105 may be used for storing a database 124. Database 124 may include a repository of determined parameters, indices and/or ratios, selectable predetermined functions, patient signal data (e.g., electrophysiological, ECG, ICEG, respiration signal data, hemodynamic or vital sign data, etc.), patient data (e.g., demographic data, pathology history, etc.), other input data and/or other derived output parameters. Patient signal data may be provided by a patient monitor 130 that is communicatively coupled to the computer system 101.

Medical treatment device 132 may be automatically and adaptively controlled by the computer system 101 in a closed-loop feedback control system. Medical treatment device 132 may include, but is not limited to, a pacing device, ablator, cardioverter, defibrillator, and so forth. Control parameters of the medical treatment device 132, such as the pacing parameter, ablation energy control, etc., may be automatically determined by computer system 101.

Patient monitor 130 may be used to acquire various types of patient signal data or information (or patient monitoring signal data). The patient signal data may include, but is not limited to, hemodynamic signal data, such as invasive and non-invasive blood pressure waveform data, SPO2 waveform data, etc. The patient monitor 130 may include appropriate biometric sensors for acquiring the patient signal data. For example, patient monitor 130 may include multi-sensor blood pressure catheter to perform a pull-back procedure to acquire multi-channel or multi-position blood pressure data. Implementations of the present framework provide ratios and/or parameters to detect, diagnose and/or quantify such patient signal data. Such output ratios and/or parameters and their associated diagnoses may be presented by a presentation device 111 (e.g., display device) or used to control the medical treatment device 132.

Cardiac tissue and related circulation system components may behave differently in different situations, resulting in different properties exhibited by hemodynamic signal data. In accordance with some implementations, signal analysis unit 122 processes hemodynamic signal data acquired by, for example, the patient monitor 130. Unlike traditional methods that use cardiac electrophysiological signals and activities (e.g., surface ECG, intra-cardiac electrogram, etc.), signal analysis unit 122 may combine multiple types of parameters and/or ratios derived from hemodynamic signal data (e.g., blood pressure, SPO2 signal data) to obtain more sensitive and reliable quantification results for diagnosing and characterizing cardiac arrhythmia or other heart chamber tissue malfunction events. Signal analysis unit 122 may utilize the similarities and/or differences of hemodynamic signal cycles in different cardiac episodes to facilitate earlier and more sensitive detection of cardiac events and pathologies.

Figure 2:
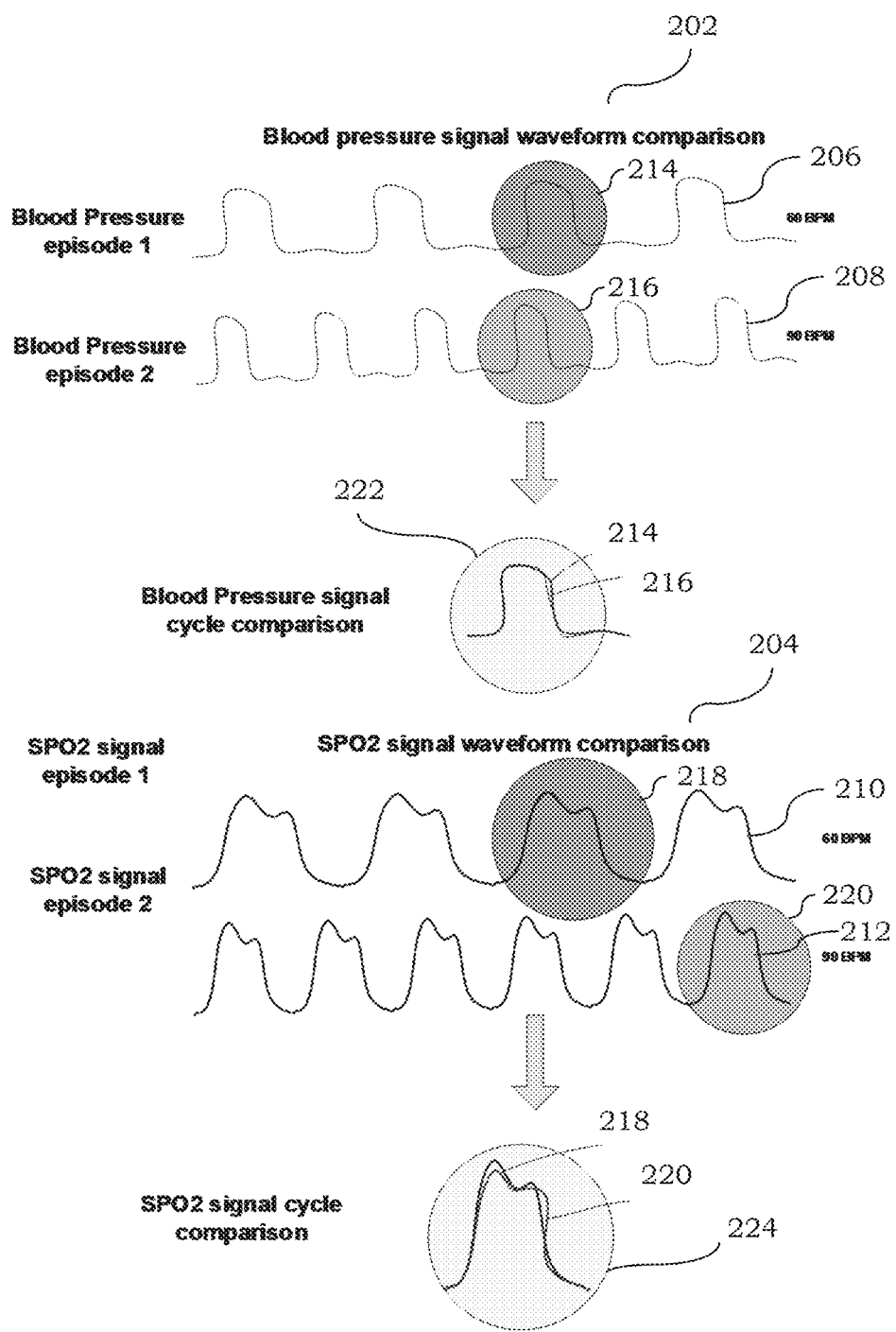
FIG. 2 shows an exemplary morphology comparison of hemodynamic signal waveforms.

FIG. 2 shows an exemplary morphology comparison of hemodynamic signal waveforms acquired during different episodes of heart rate. Two exemplary comparisons (202, 204) of non-invasive blood pressure signal data and SPO2 signal data are shown to illustrate signal mode and morphology variation and variability. Each comparison (202 or 204) is performed for two different episodes of heartbeat rates. Episode 1 involves 60 heartbeats per minute (BPM), while episode 2 involves a faster heartbeat rate of 90 BPM.

In the exemplary signal waveform comparisons (202, 204), the faster signal waveform (208 or 212) is proportionally stretched to match the time duration and amplitude of those of the slower hemodynamic signal waveform (206 or 210). From the cycle comparison (222 and 224), it can be seen that two cardiac cycles (214 and 216; 218 and 220) do not perfectly match each other. This implies that the cardiac tissue and myocardium contraction rate have some malfunctions. Such waveform stretching and matching comparison advantageously facilitates detection and characterization of early cardiac function and tissue pathologies.

Cardiac signal portion waveforms acquired during different time episodes or cardiac statuses, such as benign signal portion and cardiac arrhythmia portion (e.g. myocardial ischemia), usually show such morphology changes. However, two cardiac signal portions at two different heartbeat rates or cycle lengths may not be efficiently and effectively compared solely based on amplitude, frequency, timing latency, specific parameters and waveform indices (e.g., ST elevation, R or P wave amplitude, etc.), since the time durations are not synchronized or matched.

Implementations of the present framework perform affine template matching to determine a signal morphology affine ratio. Affine template matching may involve extracting a region of interest (ROI) from the current patient signal data, and matching the morphology (or shape) of such ROI with the reference signal portion extracted from a predetermined baseline signal portion (e.g., benign or healthy signal portion). By using such affine template matching, two different cardiac signal portions may be compared based on, for example, shape, time, amplitude, etc. Output parameters (e.g., amplitude affine ratio, energy affine ratio, cardiac cycle affine ratio, etc.) may also be determined.

Affine template matching and the associated output parameters provide a useful approach to qualitatively and quantitatively characterize hemodynamic activity related tissue functions. A biological link between cardiac tissue-function and signal waveform morphology dynamics is advantageously provided. For example, when there is myocardial ischemia and infarction in the left ventricular chamber, ventricular contraction and reperfusion mode and pattern may be distorted (e.g., prolonging of end of systolic or EoS signal portion shape, change of speed in hemodynamic signal, slowing down in EoS phase, etc.) compared with the baseline signal portion. However, the hemodynamic signal may still be functioning well with minute distortions that are not easily discernable, especially without using the affine template matching as described herein.

Figure 3:
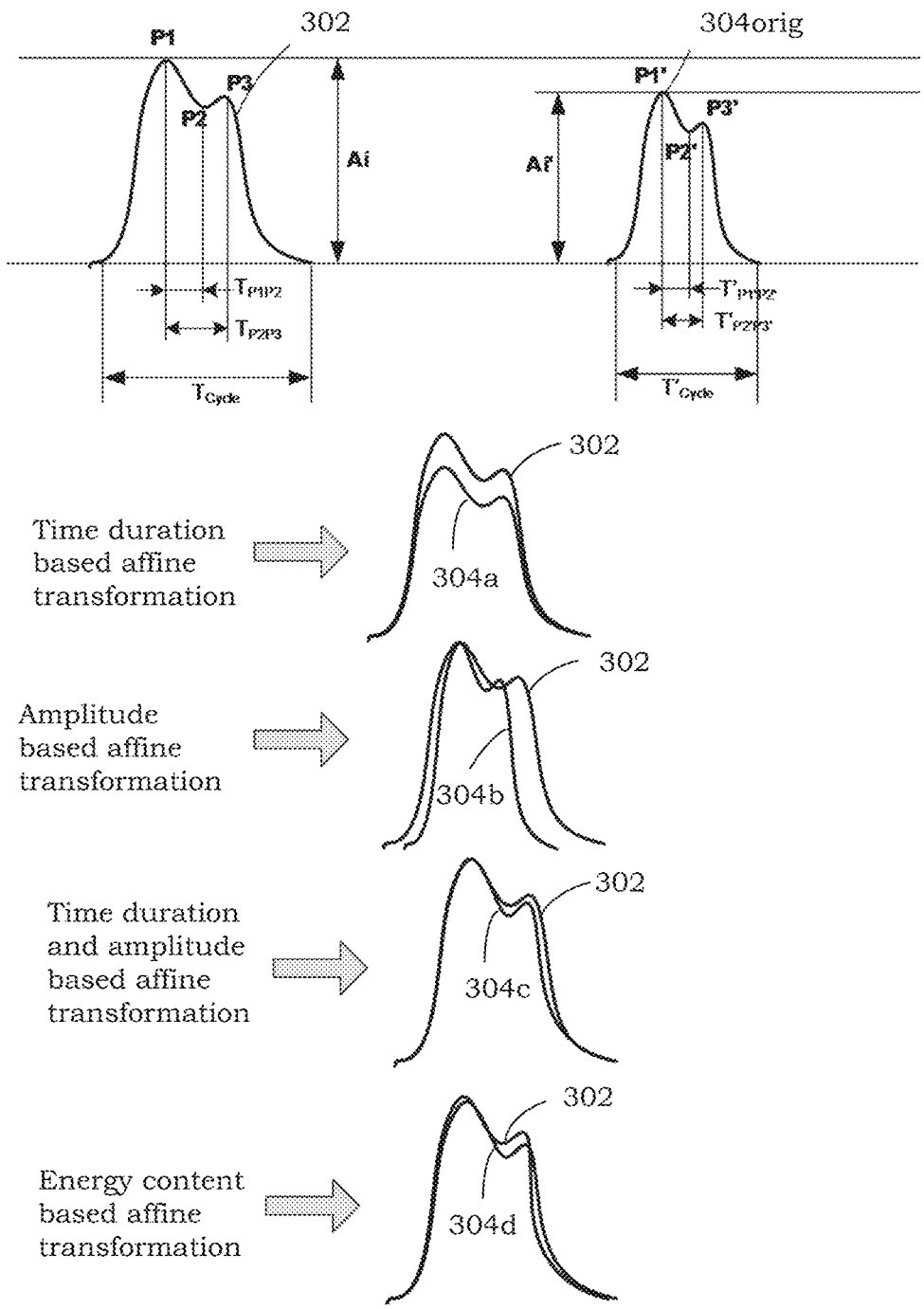
FIG. 3 shows various exemplary methods to stretch or match signal portions.

FIG. 3 shows various exemplary methods to match two signal portions (302, 304orig). The signal portions (302, 304orig) are original (pre-transform) waveforms that correspond to different cardiac statuses or episodes. In some implementations, the first signal portion (302) is extracted from a baseline (e.g., healthy or benign) hemodynamic signal while the second signal portion (304orig) is extracted from an ongoing patient monitoring hemodynamic signal. The second signal portion (304orig) may be matched with the first signal portion (302) using an affine waveform transformation method to generate a stretched signal portion (304*a-d*). An affine waveform transformation is a linear transformation that proportionally stretches or shrinks the given signal portion waveform. Different types of affine waveform transformation methods may be used. Based on the electrophysiological characteristics and/or clinical applications, the framework and/or user may automatically, semi-automatically or manually select and adjust the type of affine waveform transformation method to be used.

In some implementations, signal analysis unit 122 performs time-duration based affine waveform transformation of the second signal portion (304orig) to generate stretched signal portion (304*a*). Time-duration based affine waveform transformation stretches (or shrinks) the time duration of the second signal portion (304orig) to match the time duration of the first signal portion (302orig). Alternatively, signal analysis unit 122 may perform amplitude-based affine waveform transformation to generate stretched signal portion (304*b*). Amplitude-based affine waveform transformation matches the first and second signal portions (302, 304orig) by stretching (or shrinking) amplitudes of the second signal portion (304orig) to synchronize corresponding key points on both signal portions so that they coincide. The key point may be identified by, for example, the maximum amplitude point, the minimum amplitude point, the mean amplitude point, a peak amplitude point (shown as P1 in FIG. 3), end-of-diastolic (EoD) phase point, end-of-systolic (EoS) phase point, or other clinically meaningful point derived from the waveforms of the signal portions (302, 304orig).

As another alternative, signal analysis unit 122 may perform amplitude-time based affine waveform transformation to generate stretched signal portion (304*c*) by stretching (or shrinking) both the time duration and amplitudes of the second signal portion (304orig). As yet another alternative, signal analysis unit 122 may perform energy content (or area) based affine waveform transformation to generate stretched signal portion (304*d*) by stretching (or shrinking) the second signal portion (304orig) such that the areas under the waveforms of the first and second signal portions (302, 304*d*) substantially match.

After affine waveform transformation of the second signal portion, its waveform morphology should be similar to that of the first signal portion if there is no cardiac arrhythmia or cardiac tissue malfunction. Any mismatch or difference between the first and second signal portion waveforms may be utilized to quantify a cardiac pathology and clinical event. For example, the difference in area under the waveforms may be used to estimate blood stroke volume in heart or blood vessels, and provide a real-time output parameter for detecting and characterizing cardiac arrhythmia (e.g., myocardial ischemia and infarction).

Various methods may be used to quantify the matching rate. This process may be referred to as cardiac signal data and waveform matching pursuit, which may be utilized for pattern recognition and mode differentiation between different channels of hemodynamic signals (cross channel matching) or between hemodynamic signal waveforms of different timings associated with the same channel (mutual signal matching).

There are many mathematical methods for matching and mapping of two signal waveforms or datasets based on time duration or amplitude, such as minimum least mean errors, minimum least mean square errors (MLMSE), etc. According to the present framework, MLMSE based on key points may be used for waveform comparison. In addition to the typical MLMSE algorithm based waveform differentiation and matching comparison, there may be other methods for quantifying the waveform matching and modelling, such as through the use of statistical parameters (e.g., mutual information, mutual entropy, cross coherence, etc.). These mathematical methods may not only be useful for waveform and dataset matching tests, but they can also quantitatively detect and characterize distortions of the current recording hemodynamic signal waveform from the reference or baseline signal waveform.

Figure 4:
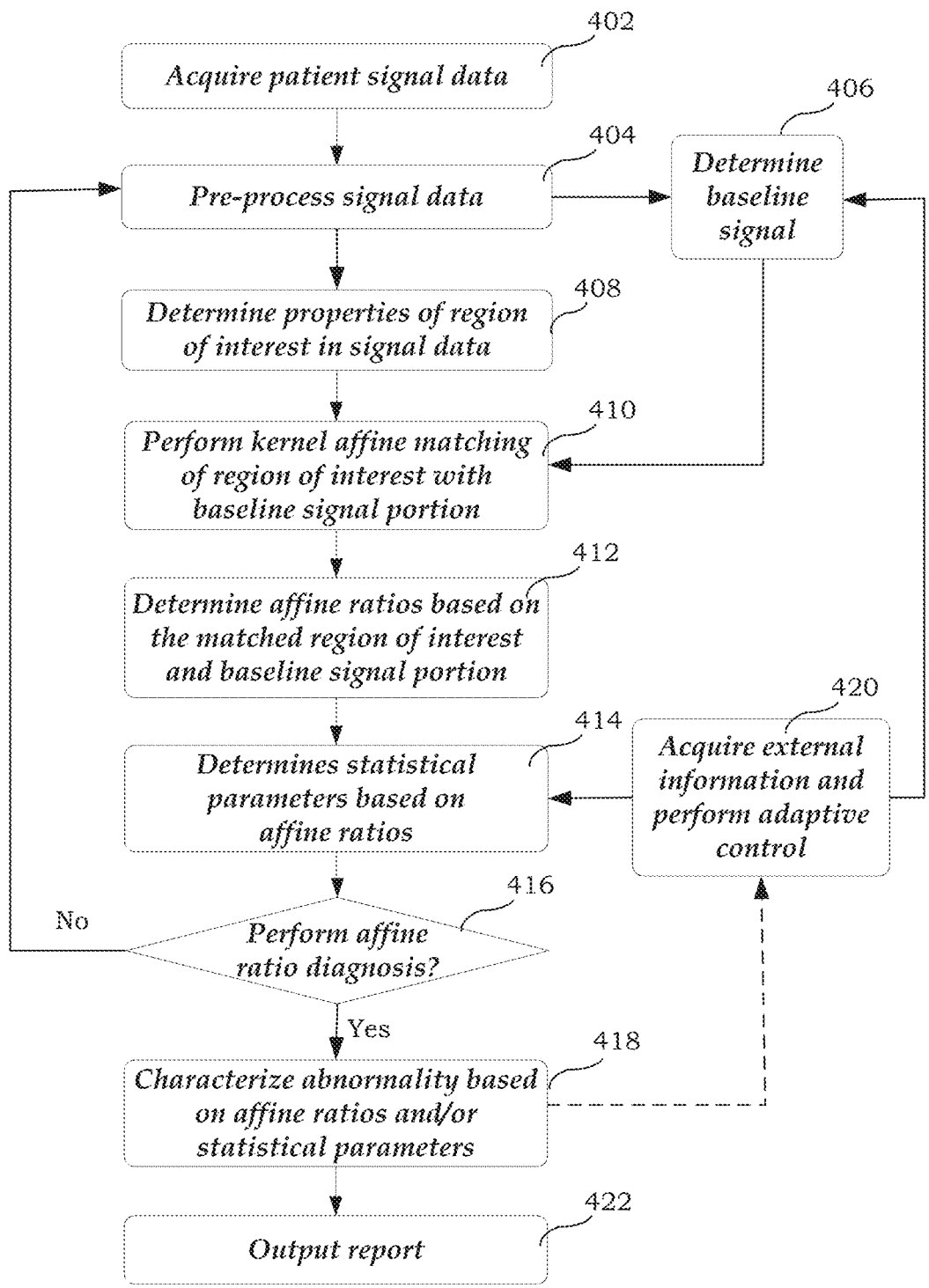
FIG. 4 shows an exemplary method of analyzing patient signal data.

FIG. 4 shows an exemplary method 400 of analyzing patient signal data. The steps of the method 400 may be performed in the order shown or a different order. Additional, different, or fewer steps may be provided. Further, the method 400 may be implemented with the system 100 of FIG. 1, a different system, or a combination thereof.

At 402, patient monitor 130 acquires ongoing patient signal data from a current patient in substantially real-time. The patient signal data may advantageously process hemodynamic signal data, such as blood pressure data, blood flow sound data, oximetric signal data (e.g., SPO2), cardiac sound data, etc., which provides better noise immunity and cardiac function analysis stability than electrophysiological signal data. Since cardiac malfunctions usually affect cardiac tissue earlier than electrophysiological characteristics would show, early detection of such minute deviations may be possible by analyzing hemodynamic signal data, not the electrophysiological signal data that is commonly used in traditional methods.

Alternatively, or additionally, other types of electrophysiological signal data, such as electrocardiogram (ECG) signal data, respiration (or capnographic) signal data and/or other vital sign signal data, other measurable patient biometric, physiological or medical signals, may also be acquired. In addition, other patient information, such as demographic data, clinical application and patient status, including, but not limited to, weight, height, gender, age, allergies, medications, pathology history, treatment history, etc., may also be acquired.

At 404, the patient signal data is pre-processed. The patient signal data may be pre-processed by conditioning, filtering, amplification, digitization and/or buffering. For example, the patient signal data may be pre-filtered and amplified for display as a waveform on, for instance, patient monitor 130. The patient signal data may be filtered to remove unwanted patient movement and respiratory artifacts, as well as power line noise. The filter may be adaptively selected in response to data indicating the current clinical application (e.g., ischemia detection application, rhythm analysis application). The patient signal data may be conditioned, amplified, buffered, filtered and/or digitized to produce a continuous stream of digitized samples.

At 406, patient signal analysis unit 122 automatically determines or selects a baseline signal from, for example, a healthy or benign portion of the digitized patient signal data or any other stored signal data. The baseline signal portion may also be region of interest prior to being affine transformed. The baseline signal generally refers to a reference signal with which the region of interest can be compared. The baseline signal is used as a reference template to match the region of interest of the ongoing patient signal data. The baseline signal may be adaptively adjusted according to the current application or clinical requirements. Alternatively, if the signal is not to be automatically determined, the user may manually select it via, for example, a user interface.

At 408, patient signal analysis unit 122 extracts a region of interest from the patient signal data and determines one or more properties of the region of interest. The region of interest may include, for example, one or more cycles extracted from the patient signal data for further analysis. The one or more properties may include, but are not limited to, heart rate, cycle length (or time duration), end of diastolic (EoD) signal amplitude, end of systolic (EoS) signal amplitude, one or more key points (e.g., maximum amplitude point, minimum amplitude point, mean amplitude point, peak amplitude point, EoD phase point, EoS phase point, etc.), and so forth.

At 410, patient signal analysis unit 122 performs kernel affine matching of the region of interest with the baseline signal portion. The patient signal data may represent different episodes at different cycle rates (or cycle time lengths). The region of interest within the patient signal data may need to be affine transformed (stretch or shrink) to best match the baseline signal waveform. Kernel affine matching involves performing an affine waveform transformation method to stretch or shrink the waveform of the region of interest to match and map to the baseline signal portion. As discussed previously, various types of affine waveform transformation methods may be used, depending on the electrophysiological characteristics and/or clinical applications. Exemplary affine waveform transformation methods include, but are not limited to, time-duration based transformation, amplitude (or key point) based transformation, time duration and amplitude based transformation, energy content based transformation, etc.

At 412, patient signal analysis unit 122 determines affine ratios based on the matched region of interest and baseline signal portion. The affine ratios facilitate comparison by quantitatively characterizing the distortion or difference between the affine transformed region of interest and the baseline signal portion. Exemplary affine ratios include, but are not limited to, affine amplitude ratio (AAR), affine timing ratio (ATR), affine shape morphology ratio (ASMR), affine template key point based discreet summary ratio (ADSR), affine template energy ratio (ATER), etc.

Figure 5:
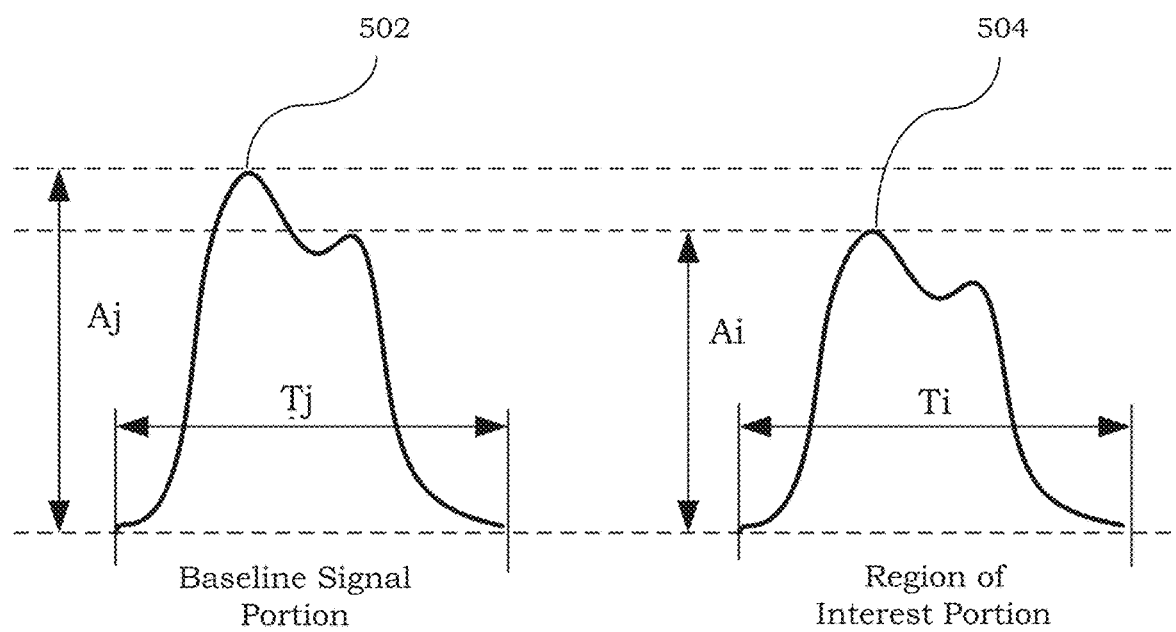
FIG. 5 illustrates an exemplary affine amplitude comparison of the baseline signal portion and the region of interest portion.

In some implementations, patient signal analysis unit 122 determines the affine amplitude ratio (AAR). The AAR may be used when the matched region of interest has a substantially similar time duration, or stretched to a substantially similar time duration, as the baseline signal portion. FIG. 5 illustrates an exemplary comparison of affine amplitude ratio (AAR) of the baseline signal portion and the region of interest portion, both of which have similar or same time durations ($T_j \approx T_i$). The time duration $T_i$ of the region of interest portion has previously been stretched to match the time duration $T_j$ of the baseline signal portion by, for example, a time-duration based stretching method as previously described.

The AAR may be determined based on amplitudes extracted from one or more key points of the waveforms of the baseline signal portion and region of interest. The key points refer to clinically significant points on the waveforms, such as the maximum amplitude point, the mean amplitude point, a peak amplitude point, end-of-diastolic (EoD) phase point, end-of-systolic (EoS) phase point, etc. These key points may be automatically selected by patient signal analysis unit 122 or manually selected by the user. A key point based AAR may be determined as follows:

$$AAR_{Key}(m) = \left| \frac{\sum\limits_{i \in baseline\_key} A_i}{\sum\limits_{j \in ROI\_key} A_j} \right| \quad (1)$$

wherein $A_j$ and $A_i$ denote amplitudes at key points (502, 504) of the baseline signal cycle waveform and the region of interest cycle waveform respectively; i and j denote indices of corresponding key points; baseline_key denotes the set of indices of all key points within the waveform of the baseline signal portion; and ROI_key denotes the set of indices of all key points within the waveform of the region of interest; and m denotes a given cardiac cycle in the patient signal data.

The AAR may also be continuously determined based on data points. The data points may be any continuous points sampled regularly along the waveforms of the baseline signal portion and region of interest. A continuous AAR may be determined as follows:

$$AAR_{Continous}(m) = \left| \frac{\sum\limits_{i \in baseline\_data} A_i}{\sum\limits_{j \in ROI\_data} A_j} \right| \quad (2)$$

wherein $A_j$ and $A_i$ denote data points (502, 504) of the baseline signal portion waveform and the region of interest waveform respectively; i and j denote indices of the data points; baseline_data denotes the set of indices of all data points within the waveform of the baseline signal portion; ROI_data denotes the set of indices of all data points within the waveform of the region of interest; and m denotes a given cardiac cycle in the patient signal data.

In some implementations, patient signal analysis unit 122 determines the affine timing ratio (ATR) based on time durations. The ATR may be used when the matched region of interest has substantially the same amplitude at a key point (e.g., maximum amplitude point) as the baseline signal portion. The amplitude of the region of interest may have previously been affine transformed to match the amplitude of the baseline signal portion as previously described.

An ATR may be determined as follows:

$$ATR(m) = \left| \frac{T_i}{T_j} \right| \text{ or } ATR_{\%}(m) = \left| \frac{T_i - T_j}{T_j} \right| \quad (3)$$

wherein ATR and $ATR_{\%}$ denote hemodynamic cycle affine timing ratio and timing difference ratio respectively; m denotes a given cardiac cycle in the patient signal data; $T_i$ denotes the time duration of a region of interest portion; $T_j$ is the time duration of the baseline signal portion, which can be adaptively re-selected or determined by the patient signal analysis unit 122 or a user.

In some implementations, patient signal analysis unit 122 determines the affine shape morphology ratio (ASMR) based on time durations and amplitudes extracted from the baseline signal portion and the matched region of interest. The ASMR may be used when both time durations and amplitudes of the matched region of interest and baseline signal cycles are substantially varying, which occur in many clinical cases. The ASMR may combine the $AAR_{Continuous}$ and ATR as follows:

$$ASMR(m) = \sqrt{AAR_{Continuos}(m)^2 + ATR(m)^2} \quad (4)$$

or $$ASMR(m) = \sqrt{AAR_{Continuos}(m)^2 + ATR_{\%}(m)^2} \quad (5)$$

In some implementations, the AAR and ATR are treated as two-dimensional parameters that are integrated as independent indices. ASMR(m) represents the signal waveform morphology and data changes in both signal dimensions (time and amplitude).

In some implementations, patient signal analysis unit 122 determines the affine template key point-based discrete summary ratio (ADSR). As compared to the ASMR, the ADSR is a discrete summary ratio that improves calculation efficiency for real-time clinical applications as by employing several ROI hemodynamic parameters at key points (e.g., maximum amplitude point, mean amplitude point, EoD phase point, EoS phase point, etc.). The simplified version of affine template matching based on key points may be utilized in implantable cardiac devices or any portable monitoring devices that have limited computation power. The ASMR may combine the $AAR_{key}$ and ATR as follows:

$$ADSR(m) = \sqrt{AAR_{Key}(m)^2 + ATR(m)^2} \quad (6)$$

or $$ADSR(m) = \sqrt{AAR_{Key}(m)^2 + ATR_{\%}(m)^2} \quad (7)$$

In some implementations, patient signal analysis unit 122 determines the affine template energy ratio (ATER). The ATER is determined based on the energy or areas covered by the waveforms of the baseline signal and region of interest. After transforming the region of interest using, for example, an energy content-based stretching method, the matched region of interest cycle has the same or similar waveform morphology as the baseline signal cycle if there is no cardiac arrhythmia or cardiac tissue malfunction. Accordingly, any mismatch or difference between the two signal waveforms (baseline and ROI) may be utilized to quantify a cardiac pathology or clinical event.

The ATER may be determined as follows:

$$ATER(m) = \left| \frac{\int_{t \in Baseline\_cycle} a(t)}{\int_{t \in Real\_time\_cycle} b(t)} \right|_{mth} \quad (8)$$

$$\text{or } ATER(m) = \left| \frac{\int_{t \in Baseline\_cycle} |a(t)|^2}{\int_{t \in Real\_time\_cycle} |b(t)|^2} \right|_{mth} \quad (9)$$

wherein ATER(m) is the affine template energy, or area, ratio for the $m^{th}$ cycle of the hemodynamic patient signal data; and a(t) and b(t) are the waveform amplitude (or magnitude) functions in the time domain for the baseline signal cycle and ROI signal cycle respectively. The two forms of affine template energy, or area ratio may be applied in different signal situations, especially when there is signal offset or shifting.

The aforementioned affine ratios may be used in different ways or variations. The affine ratios discussed thus far are determined based on waveforms of the baseline signal and the region of interest after affine waveform transformation, and may be referred to as bilateral or cross affine ratio. Affine ratios may also be determined based on the waveforms of the region of interest prior to and after stretching, and are herein referred to as unilateral affine ratios.

These affine ratios may be used independently for cardiac hemodynamic function and cardiac arrhythmia detection. Alternatively, some or all of these affine ratios may be combined in a weighted summation to generate a summary ratio, such as follows:

$$\text{Integrated\_affine\_ratio} = \sum_{p \in ROI\_affine\_ratios} \alpha_p \cdot \text{Affine\_ratio}_p \quad (10)$$

$$\text{where, } \sum_{p \in ROI\_affine\_ratios} \alpha_p = 1 \quad (11)$$

wherein Integrated_affine_ratio is the summary ratio that combines multiple affine ratios; ROI_affine_ratio is a set of the multiple affine ratios; and $\alpha_p$ is the integration calculation weight associated with the $p^{th}$ affine ratio (Affine_ratio$_p$) from the set. There may be different weights for different affine ratios. The weights may be selected according to the patient's status or clinical application significance of the respective affine ratios.

Returning to FIG. 4, at 414, patient signal analysis unit 122 determines statistical parameters based on the affine ratios. The statistical parameters may be used to adaptively and continuously characterize changes in waveform of the patient signal data. Exemplary statistical parameters include, but are not limited to, the mean, standard deviation, variability, etc.

At 416, patient signal analysis unit 122 determines if an affine ratio diagnosis is to be performed. An affine ratio diagnosis may be performed based on the affine ratios, summary ratio and/or associated statistical parameters to detect, for example, an abnormality in the blood vessel, heart, signal or cardiac function. If no diagnosis is to be performed, the method 400 returns to step 404. If diagnosis is to be performed, the method 400 proceeds to step 418.

At 418, patient signal analysis unit 122 characterizes an abnormality or event based on the affine ratios, summary ratio and/or associated statistical parameters by, for example, comparing with threshold values. The affine ratios, summary ratio and/or associated statistical parameters may also be used to automatically and adaptively generate or adjust control parameters that control the medical treatment device 132 or a user warning module. The abnormality may include, for example, cardiac arrhythmia, myocardial ischemia, vessel pathology, atrial fibrillation, atrial flutter, ventricular arrhythmias, or any other type of cardiac pathology or clinical event. In some implementations, the location, severity, type and/or timing of abnormality are determined. In order to sensitively and reliably detect the pathology, different thresholds may be utilized. For example, a myocardial event may be defined to be detected if the affine ratio value is 10% off from the baseline (or healthy) ratio value, and an infarction event may be defined to be detected if the affine ratio value is 25% off.

At 422, patient signal analysis unit 122 generates a report based on the results of the affine ratio diagnosis. The report may be presented in the form of a printed report, an electronic message (e.g., email, text message, etc.), a visualization or display, an audible or visible alert or warning, or stored in a database for future retrieval. The report may include, for example, the results of the affine ratio diagnosis and the associated affine ratios, statistical parameters and/or other information used.

At 420, patient signal analysis unit 122 optionally acquires external information and performs adaptive control. The external information can be used in determining the diagnosis, and may include, for example, the doctor's input or suggestions, patient demographic information, medical history, etc. Patient signal analysis unit 122 may also perform adaptive control by adjusting the calculation parameters, threshold, baseline signal selection, number for averaging heartbeats, etc.

Figure 6:
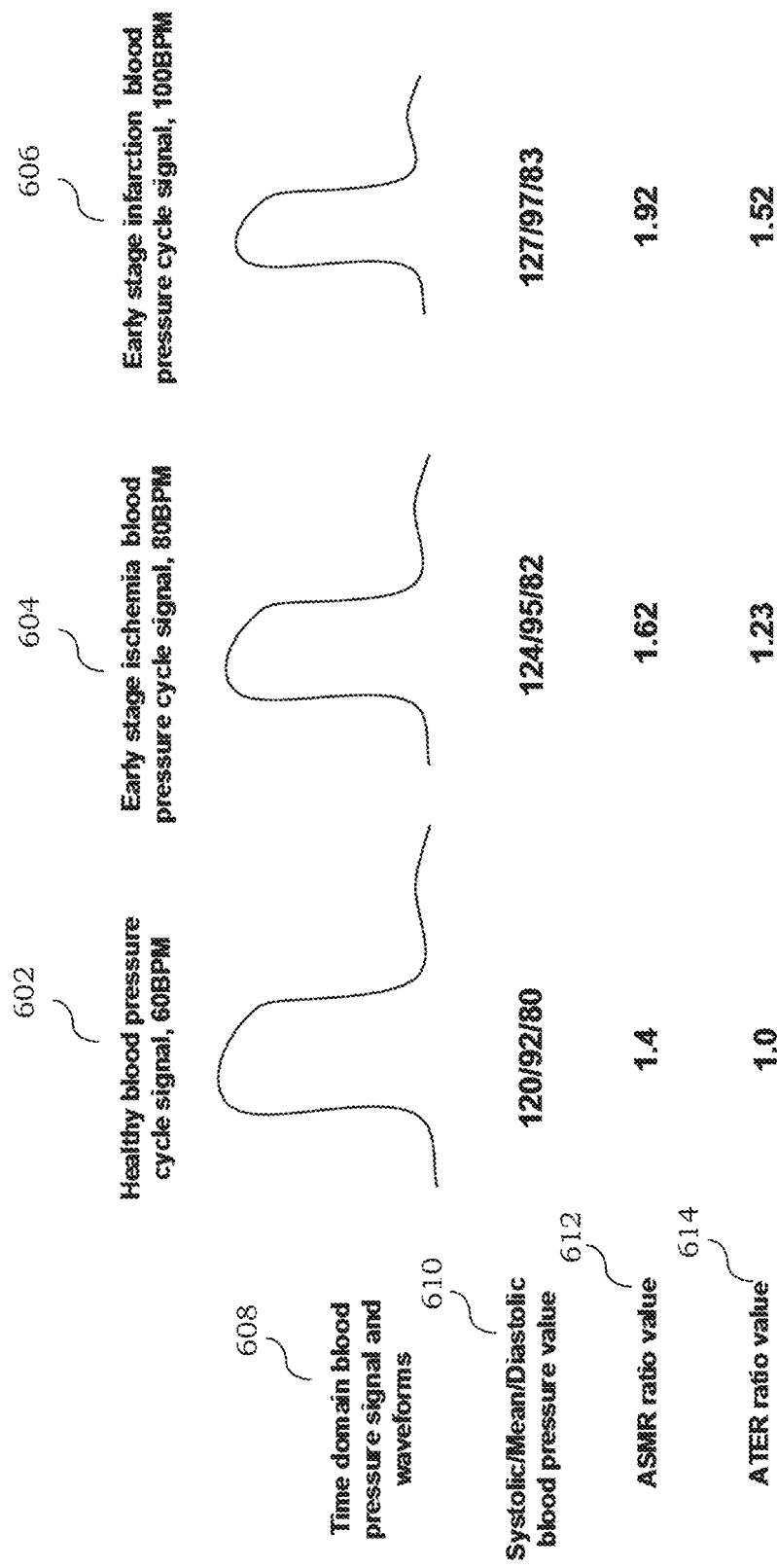
FIG. 6 shows a simulation example of myocardial ischemia event characterization based on different methods.

FIG. 6 shows a simulation example of myocardial ischemia event characterization based on different methods: blood pressure values, ASMR and ATER ratios as generated by the present framework. The methods are performed on signal data acquired during different episodes: healthy (602), early stage myocardial ischemia (604) and infarction (606) in order to show the efficiency and sensitivity of the blood pressure signal affine ratio diagnosis generated by the present framework. The blood pressure cycle lengths of the three episodes (602, 604 and 606) are different: 60 BPM (hemodynamic beats per minute), 80 BPM and 100 BPM respectively. In this simulation, a single channel intra-cardiac blood pressure signal 608 was analyzed.

Using the blood pressure value 610, there were no obvious variations to differentiate the ischemia types and severity stages. Hence, it may not be feasible to determine myocardial ischemia event information (e.g., type, location, severity, etc.) directly from the time domain blood pressure value 610.

The ASMR ratio value (612) and ATER ratio value (614) were 1.4 and 1 during the healthy episode, 1.62 and 1.23 respectively during the myocardial ischemia episode (604), and 1.92 and 1.52 respectively during the myocardial infarction episode (606). The obvious variations in the ASMR and ATER ratio values may be used to differentiate the healthy, ischemia and infarction episodes. During the ischemia episode (604), the ASMR and ATER ratio values (612, 614) changed 16% and 23% respectively, while during infarction event (606), the ASMR and ATER ratio values (612, 614) changed 37% and 52% respectively.

From this simulation, it can be observed that the variation in blood pressure signal affine ratios provided more sensitive and reliable detection than traditional blood pressure value diagnosis. Besides the qualitative analysis to identify the type of cardiac episode, the signal affine ratio analysis may also be utilized to quantitatively characterize myocardial ischemia event severity, which may greatly help clinical doctors to evaluate drug delivery and treatment strategy.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A system for patient signal analysis, comprising:
a non-transitory memory device;
a processor device in communication with the memory device; and
a signal analysis unit stored in the memory device and operative with the processor device to perform steps including
receiving hemodynamic patient signal data acquired from a patient,
extracting a region of interest from the hemodynamic patient signal data,
performing affine template matching of the region of interest with a baseline signal portion by performing an affine waveform transformation of the region of interest,
determining one or more affine ratios based on the matched region of interest and the baseline signal portion, wherein each of the one or more affine ratios quantitatively characterizes a difference between the matched region of interest and the baseline signal portion, wherein the difference quantifies a cardiac pathology,
wherein determining the one or more affine ratios comprises determining an affine amplitude ratio in response to time durations of the matched region of interest and the baseline signal portion being similar,
wherein determining the one or more affine ratios comprises determining an affine timing ratio in response to amplitudes at a key point of the matched region of interest and the baseline signal portion being similar, and
controlling a medical treatment device based at least in part on the one or more affine ratios.

2. The system of claim 1 wherein the hemodynamic patient signal data comprises blood pressure data, blood flow sound data, oximetric signal data or cardiac sound data.

3. A method of patient signal analysis, comprising:
receiving, from a patient monitor, patient signal data;
extracting, by a processor device, a region of interest from the patient signal data;
performing, by the processor device, affine template matching of the region of interest with a baseline signal portion by performing an affine waveform transformation of the region of interest;
determining, by the processor device, one or more affine ratios based on the matched region of interest and the baseline signal portion, wherein each of the one or more affine ratios quantitatively characterizes a difference between the matched region of interest and the baseline signal portion, wherein the difference quantifies a cardiac pathology,
wherein determining the one or more affine ratios comprises determining an affine amplitude ratio in response to time durations of the matched region of interest and the baseline signal portion being similar,
wherein determining the one or more affine ratios comprises determining an affine timing ratio in response to amplitudes at a key point of the matched region of interest and the baseline signal portion being similar; and
controlling, by the processor device, a medical treatment device based at least in part on the one or more affine ratios.

4. The method of claim 3 further comprising selecting the baseline signal portion from the patient signal data.

5. The method of claim 3 wherein performing the affine waveform transformation comprises stretching or shrinking a first time duration of the region of interest.

6. The method of claim 3 wherein performing the affine waveform transformation further comprises stretching or shrinking amplitudes of the region of interest to synchronize a first key point of the region of interest with a second said key point of the baseline signal portion.

7. The method of claim 6 wherein the first and second key points comprise a maximum amplitude point, a minimum amplitude point, a mean amplitude point, a peak amplitude point, an end-of-diastolic phase point or an end-of-systolic phase point.

8. The method of claim 3 wherein performing the affine waveform transformation further comprises stretching or shrinking the region of interest until waveform areas under the region of interest and the baseline signal portion match.

9. The method of claim 3 wherein determining the affine amplitude ratio comprises determining a ratio of a sum of amplitudes extracted from the baseline signal portion and a sum of amplitudes extracted from the matched region of interest.

10. The method of claim 9 wherein the amplitudes are extracted from one or more waveform key points of the baseline signal portion and the matched region of interest.

11. The method of claim 10 wherein the one or more waveform key points comprise a maximum amplitude point, a mean amplitude point, a peak amplitude point, an end-of-diastolic phase point or an end-of-systolic phase point.

12. The method of claim 9 wherein the amplitudes are extracted from continuous waveform data points of the baseline signal portion and the matched region of interest.

13. The method of claim 3 wherein determining the affine timing ratio comprises determining a ratio of time durations extracted from the baseline signal portion and the matched region of interest.

14. The method of claim 3 wherein determining the one or more affine ratios comprises determining an affine shape morphology ratio based on time durations and amplitudes extracted from continuous data points of the baseline signal portion and the matched region of interest in response to the time durations and the amplitudes of the matched region of interest and the baseline signal portion being varying, wherein determining the affine shape morphology ratio comprises integrating the affine amplitude ratio and the affine timing ratio.

15. The method of claim 3 wherein determining the one or more affine ratios comprises determining an affine template key point based discrete summary ratio based on time durations and amplitudes extracted from key points of the baseline signal portion and matched region of interest.

16. The method of claim 3 wherein determining the one or more affine ratios comprises determining an affine template energy ratio based on areas covered by waveforms of the baseline signal portion and the matched region of interest.

17. The method of claim 3 further comprising determining a weighted summation of multiple affine ratios to generate a summary ratio and outputting a report based on the summary ratio.

18. The method of claim 3 further comprising determining one or more statistical parameters based on multiple affine ratios and outputting a report based on the one or more statistical parameters.

19. A non-transitory computer readable medium embodying a program of instructions executable by machine to perform steps for patient signal analysis, the steps comprising:
   receiving, from a patient monitor, patient signal data;
   extracting, by a processor device, a region of interest from the patient signal data; performing, by the processor device, affine template matching of the region of interest with a baseline signal portion by performing an affine waveform transformation of the region of interest;
   determining, by the processor device, one or more affine ratios based on the matched region of interest and the baseline signal portion, wherein each of the one or more affine ratios quantitatively characterizes a difference between the matched region of interest and the baseline signal portion, wherein the difference quantifies a cardiac pathology,
      wherein determining the one or more affine ratios comprises determining an affine amplitude ratio in response to time durations of the matched region of interest and the baseline signal portion being similar,
      wherein determining the one or more affine ratios comprises determining an affine timing ratio in response to amplitudes at a key point of the matched region of interest and the baseline signal portion being similar; and
   controlling a medical treatment device based at least in part on the one or more affine ratios.

* * * * *